United States Patent [19]

Junino et al.

[11] Patent Number: 4,727,192

[45] Date of Patent: Feb. 23, 1988

[54] 2,4-DINITRO- OR 2-AMINO-4-NITRO- OR 2-NITRO-4-AMINO-6-HYDROXYALKYLANILINES, THE PROCESS FOR PREPARATION THEREOF AND THEIR USE IN DYEING KERATINOUS FIBERS, AND ESPECIALLY HUMAN HAIR

[75] Inventors: Alex Junino, Livry-Gargan; Gerard Lang, Saint-Gratien; Nicole Jehanno, Brunoy, all of France

[73] Assignee: L'Oreal, Paris, France

[21] Appl. No.: 808,814

[22] Filed: Dec. 13, 1985

[30] Foreign Application Priority Data

Dec. 13, 1984 [LU] Luxembourg .......................... 85679
Dec. 13, 1984 [LU] Luxembourg .......................... 85680
Dec. 13, 1984 [LU] Luxembourg .......................... 85681

[51] Int. Cl.$^4$ ................... C07C 87/60; C07C 87/28; A61K 7/13
[52] U.S. Cl. .................... 564/441; 564/367; 564/368; 564/369; 564/371; 564/443; 8/410; 8/414; 8/415
[58] Field of Search ............... 564/367, 368, 369, 371, 564/441, 443; 8/410, 414, 415

[56] References Cited

U.S. PATENT DOCUMENTS

| | | | |
|---|---|---|---|
| 3,446,567 | 5/1969 | Augustin et al. | 8/410 |
| 3,665,036 | 5/1972 | Kalopissis et al. | 260/556 AR |
| 3,794,676 | 2/1974 | Halasz | 564/441 |
| 3,867,456 | 2/1975 | Kalopissis et al. | 260/574 |
| 4,470,826 | 9/1984 | Bugaut et al. | 564/367 |

FOREIGN PATENT DOCUMENTS 1128863 8/1982 Canada .
1449648 7/1966 France .
1506350 11/1967 France .

OTHER PUBLICATIONS

Bolamm et al, "NMR Spectra of Some Nitro-Substituted N-Alkylanilines II", *Acta Chemica Scandinavica* 20 (1966), No. 5, pp. 1208–1220.

*Primary Examiner*—Charles F. Warren
*Assistant Examiner*—John A. Sopp
*Attorney, Agent, or Firm*—Fleit, Jacobson, Cohn & Price

[57] ABSTRACT

The invention relates to a compound of formula

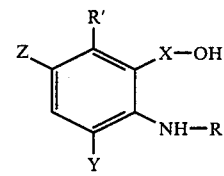

(I)

in which:

X denotes a branched or unbranched alkylene radical containing 2 to 6 carbon atoms, optionally being able to be substituted with one or more hydroxyl radicals;

R denotes a hydrogen atom, an alkyl or a mono- or polyhydroxyalkyl radical or an aminoalkyl radical in which the amine group can be mono- or disubstituted with an alkyl radical or with a mono- or polyhydroxyalkyl radical, the nitrogen atom also being able to form part of a heterocyclic system and the alkyl radicals containing 1 to 4 carbon atoms;

R' denotes a hydrogen atom or a $C_1$ to $C_4$ alkyl radical;

Y and Z denote a nitro and/or —$NHR_1$ radical, $R_1$ and R, which may be identical or different, having the meanings given above for R, with the proviso that when Y and Z are identical, they necessarily denote nitro radicals, and the cosmetically acceptable salts of the compounds containing a salifiable amine group, and also the process for preparing it and its use in dyeing keratinous fibres, and especially human hair.

23 Claims, No Drawings

2,4-DINITRO- OR 2-AMINO-4-NITRO- OR 2-NITRO-4-AMINO-6-HYDROXYALKYLANI-LINES, THE PROCESS FOR PREPARATION THEREOF AND THEIR USE IN DYEING KERATINOUS FIBERS, AND ESPECIALLY HUMAN HAIR

The present invention relates to new 2,4-dinitro- or 2-amino-4-nitro- or 2-nitro-4-amino-6-hydroxyalkylanilines, the process for preparation thereof and their use in dyeing keratinous fibres, and especially human hair, both by direct dyeing and by so-called oxidation dyeing.

It is well known that, to perform direct dyeing on hair or endow the latter with complementary glints in the case of oxidation dyeing, nitro derivatives of the benzene series can be used.

The use has already been recommended, both in direct dyeing and in oxidation dyeing, of N-substituted 2,4-dinitroanilines, which are obtained by reaction of a primary amine with 2,4-dinitro-1-chlorobenzene and also of nitro-orthophenylenediamines such as, more especially, 2-amino-4-nitro-6-alkyl-anilines or nitro-paraphenylenediamines in which the nitrogen atoms are mono- or disubstituted.

Nevertheless, said compounds when used as direct dyes for dyeing keratinous fibres, and more especially human hair, give rise to shades which are insufficiently stable to light, adverse weather conditions or washing.

Consequently, the Applicant has sought other nitroaminobenzene dyes which enable shades to be obtained which are more resistant to light, adverse weather conditions and washing, and has consequently discovered the compounds of formula:

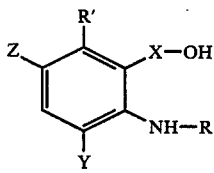

(I)

in which
X denotes a branched or unbranched alkylene radical containing 2 to 6 carbon atoms, optionally being able to be substituted with one or more hydroxyl radicals;
R denotes a hydrogen atom, an alkyl or a mono- or polyhydroxyalkyl radical or an aminoalkyl radical in which the amine group can be mono- or disubstituted with an alkyl or a mono- or polyhydroxyalkyl radical, the nitrogen atom also being able to form part of a heterocyclic system, and the alkyl radical containing 1 to 4 carbon atoms;
R' denotes a hydrogen atom or a $C_1$ to $C_4$ alkyl radical;
Y and Z denote a nitro and/or $NHR_1$ radical, $R_1$ and R, which may be identical or different, having the meanings given above for R, with the proviso that when Y and Z are identical, they necessarily denote nitro radicals.

The subject of the present invention is hence the new 2,4-dinitro-6-hydroxyalkylanilines of formula (Ia)

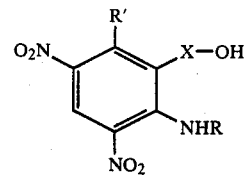

(Ia)

the new 2-amino-4-nitro-6-hydroxyalkylanilines of formula (Id)

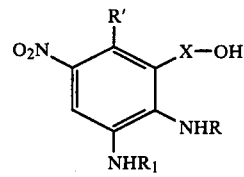

(Id)

and the new 2-nitro-4-amino-6-hydroxyalkylanilines of formula (Ie)

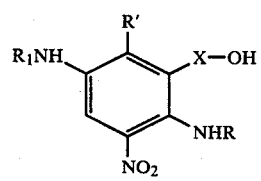

(Ie)

R', X, R and $R_1$ having the meanings given above, as well as the cosmetically acceptable salts of the compounds (Ia), (Id) and (Ie) containing one salifiable amine group.

By way of preferred radicals x, ethylene, propylene, 1,1-dimethylethylene, 1,2-dimethylethylene and 1,1,2-trimethylethylene radicals may be mentioned.

By way of preferred radicals R and $R_1$, hydrogen and methyl, ethyl, n-propyl, β-hydroxyethyl, γ-hydroxypropyl, β, γ-dihydroxypropyl, β-aminoethyl and β-diethylaminoethyl radicals may be mentioned.

By way of preferred radicals R', hydrogen and the methyl radical may be mentioned.

Preferred compounds of formula (Ia) according to the invention are the following:
2-(2-amino-3,5-dinitrophenyl)ethanol;
2-[2-(β-hydroxyethyl)amino-3,5-dinitrophenyl]ethanol;
1-(2-amino-3,5-dinitrophenyl)-2-propanol;
1-(2-methylamino-3,5-dinitrophenyl)-2-propanol;
1-[2-(β-aminoethyl)amino-3,5-dinitrophenyl]-2-propanol,
as well as the salts thereof.

Preferred compounds of formula (Id) according to the invention are the following:
2-(2,3-diamino-5-nitrophenyl)ethanol;
2-[3-amino-2-(β-hydroxyethyl)amino-5-nitrophenyl]ethanol;
1-(2,3-diamino-5-nitrophenyl)-2-propanol;
1-(3-amino-2-methylamino-5-nitrophenyl)-2-propanol,
as well as the salts thereof.

Preferred compounds of formula (Ie) according to the invention are the following:
2-(2,5-diamino-3-nitrophenyl)ethanol;
1-(2,5-diamion-3-nitrophenyl)-2-propanol;

1-[2-amino-5-(β-hydroxyethyl)amino-3-nitrophenyl]-2-propanol, as well as the salts thereof.

The subject of the invention is also the process for preparing the compounds of formula (I), which consists in reacting an aqueous ammonia solution or a primary aliphatic amine R—NH$_2$, where R has the meaning given above, with the heterocyclic compounds of formula (II), according to the following reaction scheme:

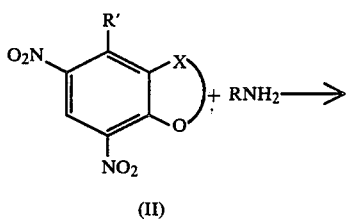

R' and X having the meaning given above to obtain a 2,4-dinitro-6-hydroxyalkylaniline of formula (Ia) which is then optionally subjected to a selective reduction to obtain a 2-amino-4-nitro-6-hydroxyalkylaniline of formula (Ib) or a 2-nitro-4-amino-6-hydroxyalkylaniline of formula (Ic), which are then optionally subjected to an alkylation, a hydroxyalkylation or an aminoalkylation according to a conventional chemical process, to obtain the final compound of formula (Id) and (Ie) respectively. To obtain the compound of formula (Ic), selective reduction is performed on the compound (Ia) in which R=H, which is obtained by reacting aqueous ammonia solution with the heterocyclic compound (II).

The scheme for the process is as follows:

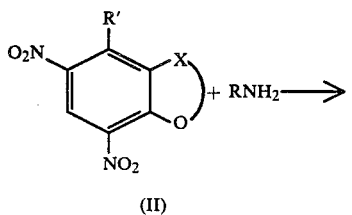

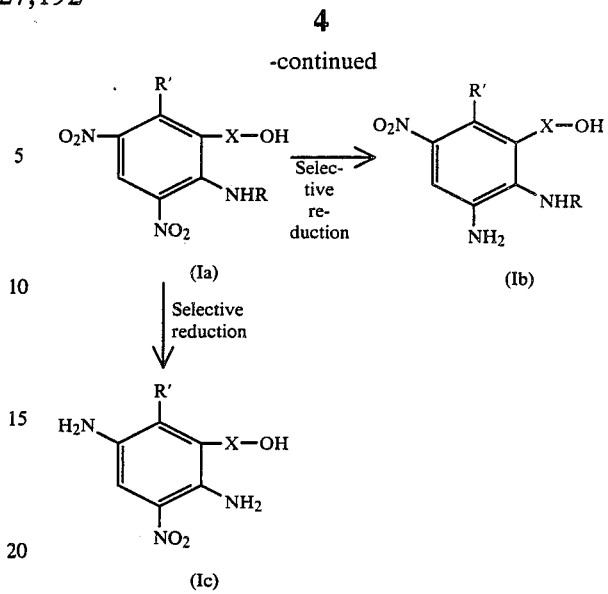

R', X and R$_1$ having the meaning given above.

The opening of the heterocyclic ring by the primary amine or by ammonia is performed at a temperature between 20° and 120° C., optionally under pressure, in the presence or absence of polar protic solvents such as water, alcohols, glycols or glycol ethers, or polar aprotic solvents such as formamide, dimethylformamide, dioxane or tetrahydrofuran.

The compounds of formula (II) are obtained by nitration of the compounds of formula (III):

where R' and X have the meaning given above, the nitration being performed by adding the compound (III) to fuming nitric acid at a temperature between 30° and 35° C. [according to G. CHATELUS—Ann. Chem. 4, 505–547 (1949)] or by adding the compound (III) to a mixture of concentrated sulphuric and nitric acids at a temperature in the region of 5° C. [according to Charles D. HURD, Rostyslaw DOWBENKO, J.A.C.S. 80, 4711–14 (1958)]; the compound (II) is then isolated after dilution of the reaction medium with water.

Compounds of formula (III) are known, and most of the compounds of formula (II) are also known.

Among the known compounds of formula (II), the following may be mentioned: 5,7-dinitrocoumaran (or 2,3-dihydro-5,7-dinitrobenzofuran), 2-methyl-5,7-dinitrocoumaran, 2,2-dimethyl-5,7-dinitrocoumaran, 2,3-dimethyl-5,7-dinitrocoumaran and 2,2,3-trimethyl-5,7-dinitrocoumaran.

The selective reduction of the compound of formula (Ia) to obtain the compound (Ib) is performed either with a hydroalcoholic solution of sodium sulphide in the presence of sulphur at a temperature between 10° and 70° C., or with hydrogen sulphide in the presence of ammonia solution according to M. KAMEL, M. I. ALI and M. M. KAMEL, TETRAHEDRON 1966, vol. 22, p. 3353, or alternatively by transfer of hydrogen from cyclohexene to the compound (Ia) in the presence of Pd/C, in $C_1$–$C_4$ lower alcohols and at a temperature between 15° C. and the boiling point, in a manner similar to that of Ian D. ENTWISTLE, Robert A. W. JOHNSTENE and Jeffery POVALL [(J. C. S. PERKIN I (1975), p. 1300].

The selective reduction of the compound of formula (Ia) in which R=H to obtain the compound (Ic) is performed by transfer of hydrogen from cyclohexene to the compound (Ia), Pd/C being used as catalyst, in the presence of alcohol, water and an inorganic acid such as concentrated hydrochloric acid.

The compounds (Ic) can also be obtained by selective reduction of the compounds (Ia) in which R=H in a polar solvent such as a $C_1$–$C_5$ alcohol, by introduction of hydrogen in the presence of a hydrogenation catalyst such as Pd/C and an aqueous solution of an inorganic acid such as HCl, $H_2SO_4$ or $H_3PO_4$, at a temperature between 20° and 90° C. This process is described in French Pat. No. 1,303,215.

The conventional processes of alkylation, hydroxyalkylation or aminoalkylation used to obtain the compounds of formulae (Id) and (Ie) from compounds (Ib) and (Ic) can, for example, be those described in French Pat. Nos. 2,348,911, 2,497,662 and 2,492,370 of the Applicant, or other conventional processes.

The process for preparing the compounds of formula (I) according to the invention enable excellent yields of these compounds to be obtained.

A further subject of the present invention consists of a dyeing composition for keratinous fibres, and more especially for human hair, containing at least one 2,4-dinitro- or one 2-amono-4-nitro- or one 2-nitro-4-amino-6-hydroxyalkylaniline of formula (Ia), (Id) or (Ie) above, or one of its cosmetically acceptable salts, in a solvent medium.

The present invention also relates to a process for dyeing keratinous fibres, and more especially human hair, by direct dyeing or by oxidation dyeing involving development with an oxidising agent.

The dyeing compositions according to the invention contain, in a solvent medium, at least one compound corresponding to the formula (I), or one of its cosmetically acceptable salts, and can be used for direct dyeing of keratinous fibres or for oxidation dyeing of these fibres, in which case the compounds of formula (I) confer glints which are complementary to the basic coloration obtained by oxidative development of precursors of oxidation dyes.

These compositions contain the compounds according to the invention in proportions of between 0.001 and 5% by weight, and preferably between 0.05 and 2% by weight, relative to the total weight of the composition.

The solvent medium is preferably a cosmetic vehicle generally consisting of water, but organic solvents can also be added into the compositions to solubilise compounds which would not be sufficiently soluble in water. Among these solvents, there may be mentioned lower alkanols such as ethanol and isopropanol, aromatic alcohols such as benzyl alcohol, polyols such as glycerol, glycols or glycol ethers such as 2-butoxyethanol or 2-ethoxyethanol, ethylene glycol and propylene glycol, diethylene glycol monomethyl ether and monoethyl ether and also similar products and mixtures thereof. These solvents are preferably present in proportions ranging from 1 to 75% by weight, and especially from 5 to 50% by weight, relative to the total weight of the composition.

These compositions can contain anionic, cationic, nonionic or amphoteric surfactants, or mixtures thereof. These surfactants are present in the compositions of the invention in proportions of between 0.5 and 55% by weight, and preferably between 4 and 40% by weight, relative to the total weight of the composition.

The compositions can be thickened, preferably with compounds chosen from sodium alginate, gum arabic, cellulose derivatives such as methylcellulose, hydroxyethylcellulose, hydroxypropylmethylcellulose and carboxymethylcellulose and various polymers which have the function of a thickener such as, more especially, acrylic acid derivatives. It is also possible to use inorganic thickening agents such as bentonite. These thickening agents are preferably present in proportions of between 0.5 and 10% by weight, and especially between 0.5 and 2% by weight, relative to the total weight of the composition.

The compositions according to the invention can also contain various adjuvants customarily used in dyeing compositions for the hair, and especially penetrants, dispersants, sequestering agents, film-forming agents, buffers and perfumes.

These compositions can take various forms such as liquid, cream or gel form, or any other form suitable for carrying out hair dyeing. They can in addition be packaged in aerosol containers in the presence of a propellant.

The pH of these dyeing compositions can be between 3 and 11.5, and preferably between 5 and 11.5. It is adjusted to the desired value using an alkalinising agent such as ammonia solution, sodium carbonate, potassium carbonate or ammonium carbonate, sodium hydroxide or potassium hydroxide, alkanolamines such as mono-, di- or triethanolamine, 2-amino-2-methyl-1-propanol, 2-amino-2-methyl-1,3-propanediol, or alkylamines such as ethylamine or triethylamine, or using an acidifying agent such as phosphoric, hydrochloric, tartaric, acetic, lactic or citric acid.

When the compositions are intended for use in a process for direct dyeing of hair, they can contain, in addition to the compounds according to the invention, other direct dyes such as azo or anthraquinone dyes, for example 1,4,5,8-tetraaminoanthraquinone, indophenols, indoanilines and nitro dyes of the benzene series other than the compounds of formula (I).

The concentrations of these direct dyes other than the dyes of formula (I) can be between 0.001 and 5% by weight relative to the total weight of the composition.

These compositions, employed in a direct dyeing process, are applied on the keratinous fibres for an exposure time which varies from 5 to 50 minutes, the fibres are then rinsed, optionally washed with shampoo, rinsed again and dried.

The compositions according to the invention can also be employed in the form of hair setting lotions intended at one and the same time to endow the hair with a light coloration or with glints, and to improve the shaperetention of the set. In this case, they take the form of aqueous, alcoholic or hydroalcoholic solutions containing at least one cosmetic resin, and they are applied on damp hair which has been washed and rinsed beforehand and which is optionally coiled and then dried.

The cosmetic resins which are used in the setting lotions can be, in particular, polyvinylpyrrolidone, crotonic acid/vinyl acetate, vinylpyrrolidone/vinyl acetate, maleic anhydride/butyl vinyl ether and maleic anhydride/methyl vinyl ether copolymers, as well as any other cationic, anionic, nonionic or amphoteric polymer customarily used in this type of composition. These cosmetic resins participate in the compositions of the invention in the proportion of 0.5 to 4% by weight, and preferably from 1 to 3% by weight, based on the total weight of the composition.

When the compositions according to the invention constitute oxidation dyes, involving development with an oxidising agent, the compounds of formula (I) according to the invention are mainly used for the purpose of contributing glints to the final dyeing.

These compositions then contain, in combination with at least one nitro dye of formula (I) and optionally other direct dyes, oxidation dye precursors.

The compositions can contain, for example, para-phenylenediamines such as: para-phenylenediamine, paratolylenediamine, 2-chloro-para-phenylenediamine, 2,6-dimethyl-para-phenylenediamine, 2,6-dimethyl-3-methoxy-paraphenylenediamine, N-(β-methoxyethyl)-para-phenylenediamine, N,N-bis(≠-hydroxyethyl)-para-phenylenediamine, 4-[N-ethyl-N-(carbamylmethyl)amino]aniline and also the salts thereof.

They can also contain para-aminophenols, for example: para-aminophenol, N-methyl-para-aminophenol, 2-chloro-4-aminophenol, 3-chloro-4-aminophenol, 2-methyl-4-aminophenol and the salts thereof.

They can also contain ortho-aminophenol.

They can also contain heterocyclic derivatives, for example: 2,5-diaminopyridine and 7-aminobenzomorpholine.

The compositions according to the invention can contain, in combination with the oxidation dye precursors, couplers which are well-known in the state of the art.

By way of couplers, there may be mentioned, in particular: meta-diphenols, meta-aminophenols and the salts thereof, meta-phenylenediamines and the salts thereof, meta-acylaminophenols, meta-ureidophenols and meta-carbalkoxyaminophenols.

As other couplers which can be used in the compositions according to the invention, there may finally be mentioned: α-naphthol, couplers possessing an active methylene group such as diketo compounds and pyrazolones, and heterocyclic couplers derived from pyridine and benzomorpholine.

These compositions contain, in addition to the oxidation dye precursors, reducing agents present in proportions of between 0.05 and 3% by weight relative to the total weight of the composition.

The oxidation dye precursors can be used, in the compositions of the invention, at concentrations of between 0.001 and 5% by weight, and preferably between 0.03 and 2% by weight, based on the total weight of the composition. The couplers can also be present in proportions of between 0.001 and 5% by weight, and preferably between 0.015 and 2% by weight. The pH of these oxidation dyeing compositions is preferably between 7 and 11.5, and is adjusted using alkalinising agents defined above.

The process of dyeing the keratinous fibres, especially human hair, employing development by an oxidising agent, consists in applying on the hair the dyeing composition containing both a dye according to the invention and dye precursors. The development of the coloration can then be accomplished slowly in the presence of the oxygen in the air, but a chemical development system is preferably used, this most frequently being chosen from hydrogen peroxide, urea peroxide and persalts. A solution of "20 volumes" hydrogen peroxide is used in particular.

When the composition with the oxidising agent has been applied on the keratinous fibres, it is left in place for 10 to 50 minutes, preferably 15 to 30 minutes, after which the keratinous fibres are rinsed, optionally washed with shampoo, rinsed again and dried.

The examples which follow are intended to illustrate the invention without being limitative in nature.

PREPARATION EXAMPLE 1

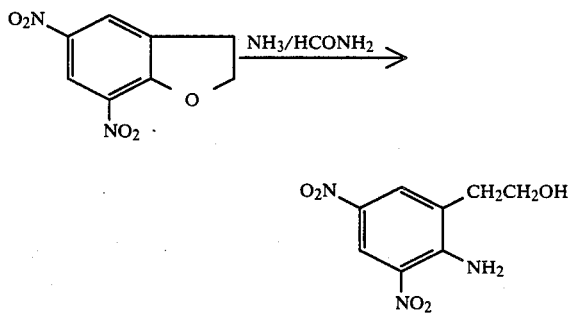

Preparation of 2-(2-amino-3,5-dinitrophenyl)ethanol 0.17 Mole (35.7 g) of 2,3-dihydro-5,7-dinitrobenzofuran, prepared according to Chatelus Ann. Chim. [12], 4,505-547 (1949), is suspended in 350 ml of 20% strength ammonia solution and 220 ml of formamide. After 8 hours' heating at 110° C., a further 100 ml of 20% strength ammonia solution are added. Heating is maintained for 4 hours. When the reaction medium is cooled, the expected product precipitates.

After being drained, washed with ice-cold water until neutral and dried under vacuum, 0.13 mole (30.3 g) of a product melting at 151° C. is obtained, and this is recrystallized from dioxane.

Analysis of the product gives the following results:

| Analysis | Calculated for $C_8H_9N_3O_5$ | Found |
| --- | --- | --- |
| % C | 42.29 | 42.24 |
| % H | 3.99 | 3.91 |
| % N | 18.50 | 18.60 |
| % O | 35.21 | 35.14 |

PREPARATION EXAMPLE 2

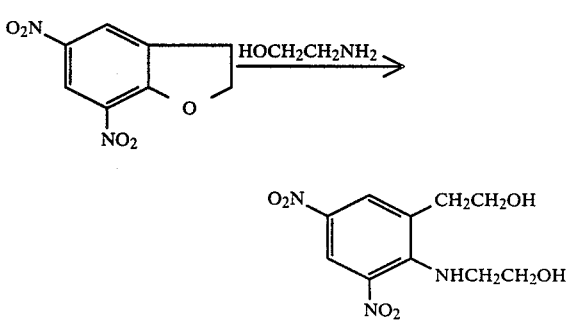

Preparation of
2-[2-(β-hydroxyethyl)amino-3,5-dinitrophenyl]ethanol 0.29 Mole (60.9 g) of 2,3-dihydro-5,7-dinitrobenzofuran is added in small portions at room temperature to 122 ml of 2-aminoethanol. After the addition is complete, the reaction medium is brought for 15 minutes to 95° C. 500 ml of water are added; after the mixture is cooled, the expected product is drained, and this, after being made into a paste in water and recrystallized from 75 ml of 96° strength ethanol, melts at 115° C.

Analysis gives the following results:

| Analysis | Calculated for $C_{10}H_{13}N_3O_6$ | Found |
| --- | --- | --- |
| % C | 44.28 | 44.38 |
| % H | 4.83 | 4.74 |
| % N | 15.49 | 15.48 |
| % O | 35.39 | 35.60 |

PREPARATION EXAMPLE 3

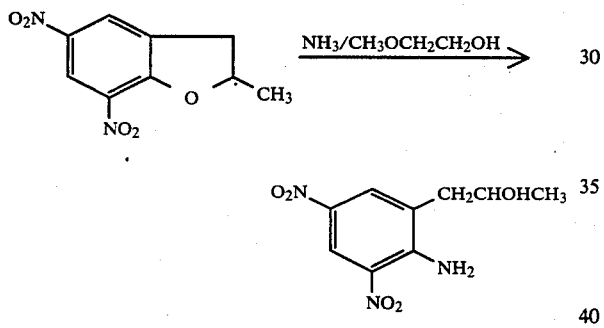

Preparation of
1-(2-amino-3,5-dinitrophenyl)-2-propanol 0.39 Mole (88 g) of 2,3-dihydro-5,7-dinitro-2-methyl-benzofuran, prepared according to J.A.C.S. 80, p. 4711–4714 (1958), is suspended in 1.1 l of 20% strength ammonia solution and 600 ml of Methyl Cellosolve. After 18 hours' heating at 70° C., the reaction mixture is cooled. The precipitate formed is drained and, after being made into a paste in water until neutral and then dried under vacuum, is recrystallized from 170 ml of dioxane. After being dried under vacuum, 0.30 mole (72 g) of the expected product is obtained; it melts at 177° C.

Analysis gives the following results:

| Analysis | Calculated for $C_9H_{11}N_3O_5$ | Found |
| --- | --- | --- |
| % C | 44.81 | 44.87 |
| % H | 4.60 | 4.62 |
| % N | 17.42 | 17.45 |
| % O | 33.17 | 33.08 |

PREPARATION EXAMPLE 4

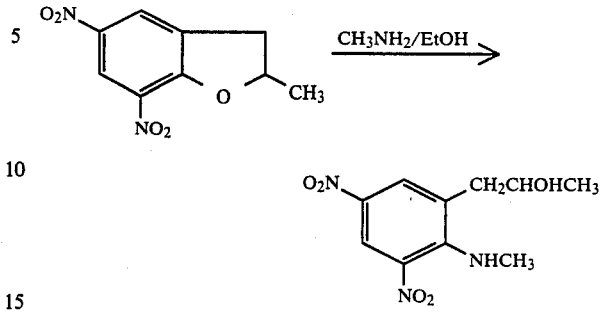

Preparation of
1-(2-methylamino-3,5-dinitrophenyl)-2-propanol 0.056 Mole (12.5 g) of 2,3-dihydro-5,7-dinitro-2-methyl-benzofuran is suspended in 100 ml of a 33% strength solution of methylamine in ethanol. After 10 hours' stirring at room temperature in a sealed Erlenmeyer, the reaction mixture is brought for 30 minutes to the refluxing temperature of the alcohol. After the mixture is cooled, the expected product precipitates. It is drained, washed with alcohol and then recrystallized from 50 ml of 96° strength ethanol. After being dried, 0.047 mole (12 g) is obtained of a product which melts at 132° C.

Analysis gives the following results:

| Analysis | Calculated for $C_{10}H_{13}N_3O_5$ | Found |
| --- | --- | --- |
| % C | 47.06 | 47.11 |
| % H | 5.13 | 5.03 |
| % N | 16.47 | 16.52 |
| % O | 31.34 | 31.25 |

PREPARATION EXAMPLE 5

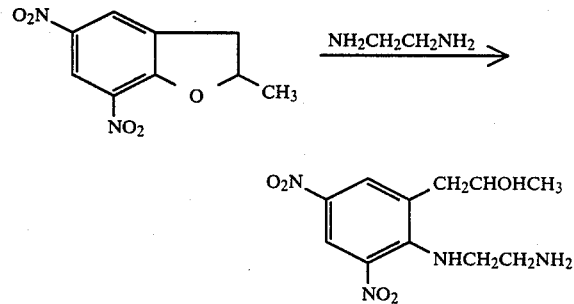

Preparation of
1-[2-(β-aminoethyl)amino-3,5-dinitrophenyl]-2-propanol 0.089 Mole (20 g) of 2,3-dihydro-5,7-dinitro-2-methylbenzofuran is added with stirring at room temperature to 40 ml of ethylenediamine. When the addition is complete, the reaction medium is poured into 500 ml of water. The expected product precipitates. After being drained and made into a paste in water, it is recrystallized from 210 ml of 96° strength ethanol. 0.074 mole (20.9 g of a product is obtained which melts at 140° C.

Molecular mass calculated for $C_{11}H_{16}N_4O_5$: 284.

Molecular mass found by potentiometric assay in acetic acid using perchloric acid: 293.

Analysis of the product obtained gives the following results:

| Analysis | Calculated for $C_{11}H_{16}N_4O_5$ | Found |
|---|---|---|
| % C | 46.47 | 46.40 |
| % H | 5.67 | 5.68 |
| % N | 19.71 | 19.82 |
| % O | 28.14 | 27.95 |

PREPARATION EXAMPLE 6

Preparation of 2-(2,3-diamino-5-nitrophenyl)ethanol

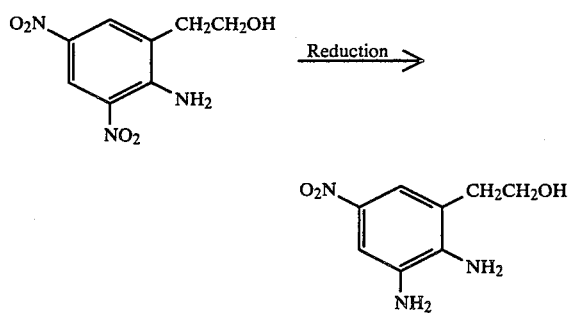

To a suspension of 0.119 mole (27 g) of 2-(2-amino-3,5-dinitrophenyl)ethanol obtained in Example 1 in 67.5 ml of isopropanol to which an equal volume of water has been added, a solution of 38.4 g of sodium sulphide nonahydrate and 5.4 g of sulphur in 10 ml of water is added dropwise at 60°–65° C. Heating is maintained for 20 minutes after the addition is complete. When the mixture is cooled, a precipitate of the expected product is obtained, and this is drained, made into a paste in water and then recrystallized from 96° strength alcohol. It melts at 172° C.

Molecular mass calculated for $C_8H_{11}N_3O_3$: 197

Molecular mass found by potentiometric assay in acetic acid using perchloric acid: 202.

Analysis of the product obtained gives the following results:

| Analysis | Calculated for $C_8H_{11}N_3O_3$ | Found |
|---|---|---|
| % C | 48.72 | 48.84 |
| % H | 5.62 | 5.71 |
| % N | 21.31 | 21.40 |
| % O | 24.34 | 24.30 |

PREPARATION EXAMPLE 7

Preparation of 2-[3-amino-2-($\beta$-hydroxyethyl)amino-5-nitrophenyl]ethanol

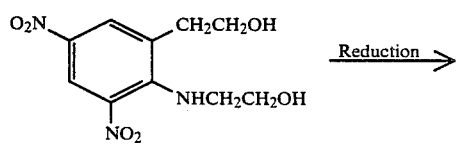

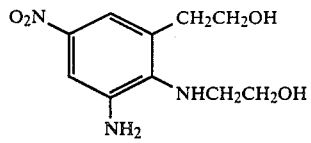

After 0.14 mole (38 g) of 2-[2-($\beta$-hydroxyethyl)amino-3,5-dinitrophenyl]ethanol, obtained in Example 2, has been added to 530 ml of absolute alcohol to which 56 ml of 20% strength ammonia solution have been added, hydrogen sulphide is bubbled into this alcoholic solution for 2 hours; the temperature rises to 27° C. The bubbling is then stopped. The reaction medium is brought to reflux for 4 hours and then left for 48 hours at room temperature. After concentration of the alcoholic solution to one half, the inorganic salts are filtered off. The filtrate is then evaporated to dryness. The dry residue is made into a paste in isopropanol. After recrystallization in order to remove a resin, the produce melts at 121° C.

Molecular mass calculated for $C_{10}H_{15}N_3O_4$: 241

Molecular mass found by potentiometric assay in acetic acid using perchloric acid: 247

Analysis of the product obtained gives the following results:

| Analysis | Calculated for $C_{10}H_{15}N_3O_4$ | Found |
|---|---|---|
| % C | 49.78 | 49.87 |
| % H | 6.27 | 6.27 |
| % N | 17.42 | 17.38 |
| % O | 26.53 | 26.25 |

PREPARATION EXAMPLE 8

Preparation of 1-(2,3-diamino-5-nitrophenyl)-2-propanol

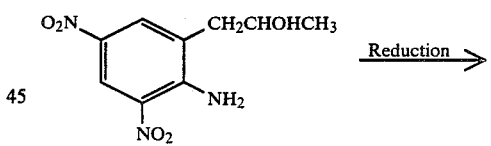

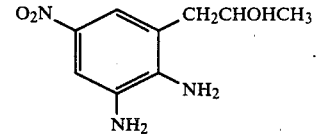

To a suspension of 0.1 mole (24.1 g) of 1-(2-amino-3,5-dinitrophenyl)-2-propanol, obtained in Example 3, in 60 ml of isopropanol to which an equal volume of water has been added, a solution of 33.6 g of sodium sulphide nonahydrate and 4.8 g of sulphur in 9 ml of water is added dropwise at 60° C.

Heating is maintained for 20 minutes after the addition is complete. When the mixture is cooled, the expected product is obtained, and this is drained, made into a paste in water and recrystallized in 96° strength ethanol. It melts at 174° C.

Molecular mass calculated for $C_9H_{13}N_3O_3$: 211

Molecular mass found by potentiometric assay in acetic acid using perchloric acid: 216.

Analysis of the product obtained gives the following results:

| Analysis | Calculated for $C_9H_{13}N_3O_3$ | Found |
|---|---|---|
| % C | 51.17 | 51.09 |
| % H | 6.20 | 6.19 |
| % N | 19.90 | 20.13 |
| % O | 22.73 | 22.57 |

PREPARATION EXAMPLE 9

Preparation of 1-(3-amino-2-methylamino-5-nitrophenyl)-2-propanol monohydrochloride

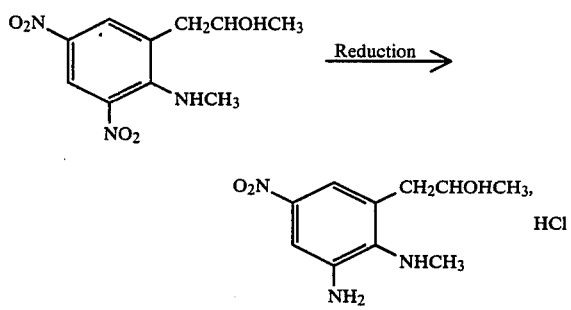

After 0.027 mole (6.88 g) of 1-(2-methylamino-3,5-dinitrophenyl)-2-propanol, obtained in Example 4, has been added to 100 ml of absolute ethanol to which 10.8 ml of 20% strength ammonia solution have been added, hydrogen sulphide is bubbled into the mixture for 2 h 30 min. After 1 hour, the temperature rises to 35° C. and then drops again. After the alcoholic solution is concentrated to one half, the inorganic salts are filtered off. The filtrate is evaporated to dryness; the dry extract in oily form is taken up with a solution of hydrochloric acid in absolute ethanol. On dilution with ethyl ether, the monohydrochloride of the expected product is obtained, and this is recrystallized from a hydroalcoholic mixture.

Molecular mass calculated for $C_{10}H_{16}N_3O_3Cl$: 261.

Molecular mass found by potentiometric assay in water using sodium hydroxide: 264.

Analysis of the product obtained gives the following results:

| Analysis | Calculated for $C_{10}H_{16}N_3O_3Cl$ | Found |
|---|---|---|
| % C | 45.89 | 46.00 |
| % H | 6.12 | 6.13 |
| % N | 16.06 | 16.21 |
| % O | 18.35 | 18.38 |
| % Cl | 13.57 | 13.64 |

PREPARATION EXAMPLE 10

Preparation of 2-(2,5-diamino-3-nitrophenyl)ethanol

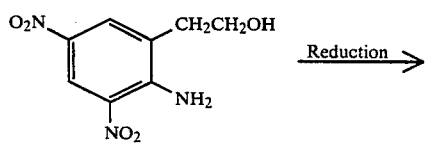

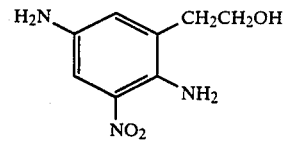

To a suspension of 15.7 g of Pd/C (containing 10% Pd) in 290 ml of absolute ethanol to which 35 ml of concentrated hydrochloric acid and 64 ml of cyclohexene have been added, 0.141 mole (32 g) of 2-(2-amino-3,5-dinitrophenyl)ethanol, obtained according to Example 1, is added. After 1 h 45 min of heating under reflux, the reaction medium is filtered hot to remove the catalyst. The filtrate is evaporated to dryness under vacuum and the dry extract, after being washed with absolute ethanol, is solubilised hot in water. 15 ml of 20% strength ammonia solution are added. When the mixture is cooled to a red precipitate of the expected product is obtained, and this, after being drained is recrystallized from Methyl Cellosolve. After being dried, the product melts at 190° C.

Molecular mass calculated for $C_8H_{11}N_3O_3$: 197.

Molecular mass found by potentiometric assay in acetic acid using perchloric acid: 199.5.

Analysis of the product obtained gives the following results:

| Analysis | Calculated for $C_8H_{11}N_3O_3$ | Found |
|---|---|---|
| % C | 48.72 | 48.88 |
| % H | 5.62 | 5.67 |
| % N | 21.31 | 21.33 |
| % O | 24.34 | 24.60 |

PREPARATION EXAMPLE 11

Preparation of 1-(2,5-diamino-3-nitrophenyl)-2-propanol

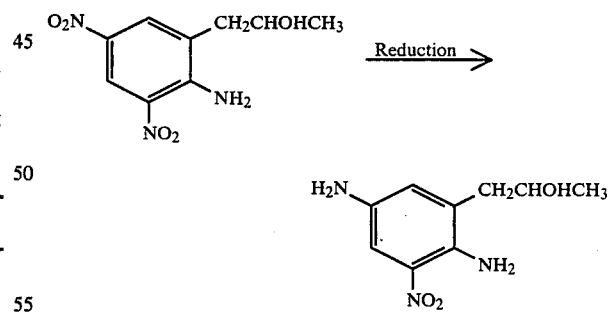

To a suspension of 5.6 g of Pd/C (containing 10% Pd) in 100 ml of absolute ethanol to which 12.5 ml of concentrated hydrochloric acid and 23 ml of cyclohexene have been added, 0.05 mole (12.05 g) of 1-(2-amino-3,5-dinitrophenyl)-2-propanol, obtained according to Example 3, is added. After 3 hours' heating under reflux, the reaction medium is filtered hot to remove the catalyst. The filtrate is evaporated to dryness, and the dry extract is made into a paste in an ethanol/ethyl ether mixture and then solubilised hot in the minimum of water. 15 ml of 20% strength ammonia solution are added in order to displace the hydrochloride. The expected product precipitates. After being drained, washed with water and recrystallized from 96° strength ethanol, it melts at 168° C.

Molecular mass calculated for C$_9$H$_{13}$N$_3$O$_3$: 211

Molecular mass found by potentiometric assay in acetic acid using perchloric acid: 210.

Analysis of the product obtained gives the following results:

| Analysis | Calculated for C$_9$H$_{13}$N$_3$O$_3$ | Found |
|---|---|---|
| % C | 51.17 | 51.31 |
| % H | 6.20 | 6.21 |
| % N | 19.90 | 20.03 |
| % O | 22.73 | 22.66 |

PREPARATION EXAMPLE 12

Preparation of 1-[2-amino-5-(β-hydroxyethyl)amino-3-nitrophenyl]-2-propanol

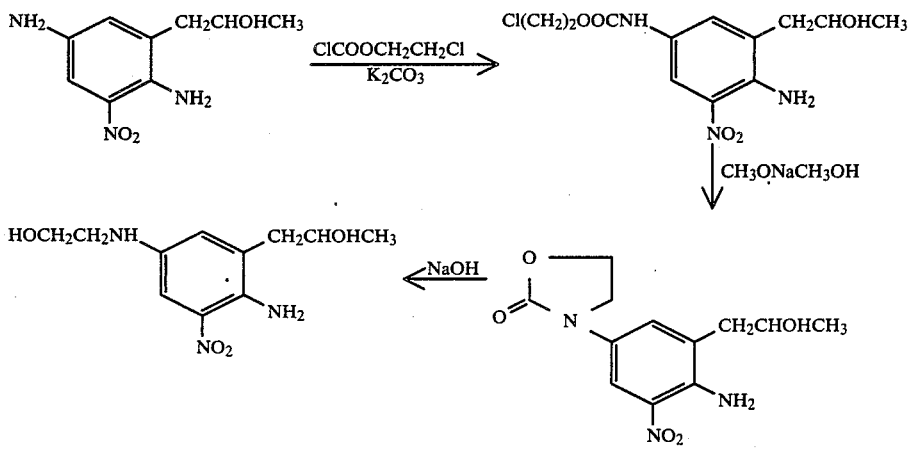

1st stage

Preparation of β-chloroethyl[4-amino-5-(β-hydroxypropyl)-3-nitrophenyl]carbamate 0.07 Mole (14.8 g) of 1-(2,5-diamino-3-nitrophenyl)-2-propanol, obtained in Preparation Example 11, is dissolved in 59 ml of dioxane to which 22 ml of water have been added. 0.0385 Mole (5.3 g) of potassium carbonate is added. The temperature is raised to 90° C., and then 0.077 mole (11 g) β-chloroethyl chloroformate is then introduced in small portions with stirring. When the addition is complete, the reaction mixture is poured onto 400 g of a water/ice mixture. The expected product precipitates; after being drained and dried under vacuum, 21.8 g of the expected product are obtained. It melts at 115° C.

2nd stage

Preparation of N-[4-amino-5-(β-hydroxypropyl)-3-nitrophenyl]oxazolidone 0.056 Mole (17.8 g) of β-chloroethyl[4-amino-5-(62-hydroxypropyl)-3-nitrophenyl]carbamate is suspended in 107 ml of 96° strength alcohol. 12 ml of a solution of sodium methylate at 30% strength in methanol are added dropwise, the temperature being maintained at 10° C. After being drained and made into a paste in water, 0.041 mole (11.6 g) of the expected product is obtained.

3rd stage

Preparation of 1-[2-amino-5-(β-hydroxyethyl)amino-3-nitrophenyl]-2-propanol 0.041 Mole (11.5 g) of N-[4-amino-5-(β-hydroxypropyl)-3-nitrophenyl]oxazolidone is introduced into 46 ml of 96° strength alcohol. The temperature is raised to 85° C. and 8.2 ml of 10N sodium hydroxide solution is poured in dropwise. Heating is maintained for 15 minutes after the addition is complete. After filtration, the filtrate is evaporated to dryness and the residue is then taken up with 40 ml of water. The expected product crystallizes; after recrystallization from water, it melts at 130° C.

Molecular mass calculated for C$_{11}$H$_{17}$N$_3$O$_4$: 255

Molecular mass found by potentiometric assay in acetic acid using perchloric acid: 256.

Analysis of the product obtained gives the following results:

| Analysis | Calculated for C$_{11}$H$_{17}$N$_3$O$_4$ | Found |
|---|---|---|
| % C | 51.75 | 51.80 |
| % H | 6.71 | 6.70 |
| % N | 16.46 | 16.62 |
| % O | 25.07 | 25.18 |

EXAMPLE 1

The following dyeing composition is prepared:

| | |
|---|---|
| 2-(2-Amino-3,5-dinitrophenyl)ethanol | 0.2 g |
| 96° strength alcohol | 15 g |
| ALFOL C$_{16/18}$ | 8 g |
| Lanette Wax E | 0.5 g |
| CEMULSOL B | 1 g |
| Oleic diethanolamide | 1.5 g |
| Triethanolamine, 1% concentration by weight | 1 g |
| Water q.s. | 100 g |
| pH 8.4 | |

When applied for 30 minutes at 28° C. on hair which has been bleached white, this mixture endows it, after shampooing and rinsing, with a coloration 6.25 Y 8.5/6, according to Munsell's notation.

EXAMPLE 2

The following dyeing composition is prepared:

| | |
|---|---|
| 2-[2-(β-Hydroxyethyl)amino-3,5-dinitro- | 0.36 g |

-continued

| | |
|---|---|
| phenyl]ethanol | |
| 2-Butoxyethanol | 10 g |
| ALFOL C$_{16/18}$ | 8 g |
| Lanette Wax E | 0.5 g |
| CEMULSOL B | 1 g |
| Oleic diethanolamide | 1.5 g |
| Triethanolamine, 1% concentration by weight | 1 g |
| Water q.s. | 100 g |
| pH 7.8 | |

When applied on hair for 20 minutes at 28° C., this mixture endows it, after shampooing and rinsing, with a coloration:
5 Y 8.5/7 on hair which has been bleached white;
5 y 8/5 on hair which is naturally 90% white, these colors being expressed according to Munsell's notation.

EXAMPLE 3

The following dyeing composition is prepared:

| | |
|---|---|
| 1-(2-Amino-3,5-dinitrophenyl)-2-propanol | 0.24 g |
| Propylene glycol | 10 g |
| COMPERLAN KD | 2.2 g |
| Lauric acid | 0.8 g |
| 2-Ethoxyethanol | 2 g |
| Monoethanolamine | 1 g |
| Water q.s. | 100 g |
| pH 8.4 | |

When applied for 30 minutes at 28° C. on hair which has been bleached white, this mixture endows it, after shampooing and rinsing, with a coloration 3.75 Y 8.5/5 according to Munsell's notation.

EXAMPLE 4

The following dyeing composition is prepared:

| | |
|---|---|
| 1-(2-Methylamino-3,5-dinitrophenyl)-2-propanol | 0.36 g |
| 96° strength alcohol | 12 g |
| COMPERLAN KD | 2.2 g |
| Lauric acid | 0.8 g |
| 2-Ethoxyethanol | 2 g |
| Monoethanolamine | 1 g |
| Water q.s. | 100 g |
| pH 8 | |

When applied for 20 minutes at 30° C. on hair which has been bleached white, this mixture endows it, after shampooing and rinsing, with a coloration 7 Y 8.5/4 according to Munsell's notation.

EXAMPLE 5

The following dyeing composition is prepared:

| | |
|---|---|
| 1-[2-($\beta$-Aminoethyl)amino-3,5-dinitrophenyl]-2-propanol | 0.12 g |
| 2-Butoxyethanol | 8 g |
| CARBOPOL 934 | 2 g |
| 2-Amino-2-methyl-1-propanol in 25% strength solution in water | 2 g |
| Water q.s. | 100 g |
| pH 5 | |

When applied for 30 minutes at 30° C. on hair which has been bleached white, this mixture endows it, after shampooing and rinsing, with a coloration 5 Y 8.5/7 according to Munsell's notation.

EXAMPLE 6

The following dyeing composition is prepared:

| | |
|---|---|
| 1-[2-($\beta$-Aminoethyl)amino-3,5-dinitrophenyl]-2-propanol | 0.415 g |
| 3-Nitro-4-methylamino-N,N—bis($\beta$-hydroxyethyl)aniline | 0.155 g |
| 2-Methyl-4-amino-3-nitro-N—($\beta$-hydroxyethyl)aniline | 0.08 g |
| 96° strength alcohol | 12 g |
| ALFOL C$_{16/18}$ | 8 g |
| Lanette Wax E | 0.5 g |
| CEMULSOL B | 1 g |
| Oleic diethanolamide | 1.5 g |
| Monoethanolamine in 20% strength solution in water | 0.25 g |
| Water q.s. | 100 g |
| pH 9.4 | |

When applied for 20 minutes at 28° C. on bleached hair, this mixture endows it, after shampooing and rinsing with a hazel coloration.

EXAMPLE 7

The following dyeing composition is prepared:

| | |
|---|---|
| 2-[2-($\beta$-hydroxyethyl)amino-3,5-dinitrophenyl]ethanol | 0.47 g |
| 3-Nitro-4-($\beta$-hydroxyethyl)aminophenol | 0.13 g |
| 1,4,5,8-Tetraaminoanthraquinone (Cibacete microdisperse blue) | 0.08 g |
| 2-Butoxyethanol | 10 g |
| CELLOSIZE WP 03 | 2 g |
| (Tallow alkyl)dimethylhydroxyethylammonium chloride | 2 g |
| 5% strength ammonia solution | 0.15 g |
| Water q.s. | 100 g |
| pH 8 | |

When applied for 25 minutes at 28° C. on bleached hair, this mixture endows it, after shampooing and rinsing, with a golden dark blonde coloration.

EXAMPLE 8

The following dyeing composition is prepared:

| | |
|---|---|
| 2-[2-($\beta$-Hydroxyethyl)amino-3,5-dinitrophenyl]ethanol | 0.205 g |
| Para-phenylenediamine | 0.08 g |
| Para-aminophenol | 0.06 g |
| Resorcinol | 0.085 g |
| Meta-aminophenol | 0.06 g |
| 3-($\beta$-Hydroxyethyl)amino-6-methylphenol | 0.05 g |
| Polyglycerolated oleic alcohol (2 moles of glycerol) | 4.5 g |
| Polyglycerolated oleic alcohol (4 moles of glycerol) | 4.5 g |
| ETHOMEEN TO 12 | 4.5 g |
| COMPERLAN KD | 9 g |
| Propylene glycol | 4 g |
| 2-Butoxyethanol | 8 g |
| 96° ethanol | 6 g |
| MASQUOL DTPA | 2 g |
| Thioglycolic acid | 0.6 g |
| Ammonia solution, 22° Be | 10 g |
| Water q.s. | 100 g |
| pH 10.5 | |

At the time of use, 100 g of "20 volumes" hydrogen peroxide are added.

When applied for 25 minutes at 30° C. on bleached hair, the mixture endows it, after shampooing and rinsing, with a golden chestnut coloration.

EXAMPLE 9

The following dyeing composition is prepared:

| | |
|---|---|
| 2-(2,3-Diamino-5-nitrophenyl)ethanol | 0.15 g |
| Propylene glycol | 10 g |
| CEMULSOL NP 4 | 12 g |
| CEMULSOL NP 9 | 15 g |
| Polyglycerolated oleic alcohol (2 moles of glycerol) | 1.5 g |
| Polyglycerolated oleic alcohol (4 moles of glycerol) | 1.5 g |
| Monoethanolamine in a 20% strength solution in water | 1.5 g |
| Water q.s. | 100 g |
| pH 10 | |

When applied on hair for 20 minutes at 28° C., this mixture endows it, after shampooing and rinsing, with a coloration:
10 YR 7.5/8 on hair bleached white:
5 Y 8/6 on hair which is naturally 90% white, these colours being expressed according to Munsell's notation.

EXAMPLE 10

The following dyeing composition is prepared:

| | |
|---|---|
| 1-(2,3-Diamino-5-nitrophenyl)-2-propanol | 0.51 g |
| 2-Butoxyethanol | 10 g |
| TWEEN 80 | 12 g |
| Oleic acid | 20 g |
| 2-Amino-2-methyl-1-propanol at 25% strength in water | 6 g |
| Water q.s. | 100 g |
| pH 6.4 | |

When applied on hair for 15 minutes at 30° C., this mixture endows it, after shampooing and rinsing, with a coloration:
10 R 6/9 on hair bleached white
7.5 YR 7/4 on hair which is naturally 90% white, these colours being expressed according to Munsell's notation.

EXAMPLE 11

The following dyeing composition is prepared:

| | |
|---|---|
| 1-(2,3-Diamino-5-nitrophenyl)-2-propanol | 0.4 g |
| 2-Butoxyethanol | 12 g |
| Carboxymethylcellulose | 2 g |
| Ammonium lauryl sulphate | 5 g |
| Triethanolamine in 1% strength solution in water | 1.5 g |
| Water q.s. | 100 g |
| pH 7.5 | |

When applied on hair for 20 minutes at 30° C., this mixture endows it, after shampooing and rinsing, with a coloration:
6.25 YR 6/15 on hair bleached white
1.25 Y 8/13 on hair which is naturally 90% white, these colours being expressed according to Munsell's notation.

EXAMPLE 12

The following dyeing composition is prepared:

| | |
|---|---|
| 1-(3-Amino-2-methylamino-5-nitrophenyl)- | 0.26 g |
| 2-propanol | |
| 96° strength alcohol | 1.0 g |
| Lauramide | 1.5 g |
| Lauric acid | 1 g |
| CELLOSIZE WP 03 | 5 g |
| Monoethanolamine | 2 g |
| Water q.s. | 100 g |
| pH 9.75 | |

When applied on hair for 20 minutes at 30° C., this mixture endows it, after shampooing and rinsing with a coloration:
5.5 YR 7/10 on hair bleached white
10 YR 7/6 on hair which is naturally 90% white, these colours being expressed according to Munsell's notation.

EXAMPLE 13

The following dyeing composition is prepared:

| | |
|---|---|
| 2-(2,3-Diamino-5-nitrophenyl)ethanol | 0.6 g |
| 2-Methyl-4-amino-5-nitro-N—(β,γ-dihydroxypropyl)aniline | 0.17 g |
| 3-Nitro-4-(β-aminoethyl)amino-N,N—bis(β-hydroxyethyl)aniline dihydrochloride | 0.12 g |
| COMPERLAN KD | 2.2 g |
| Lauric acid | 0.8 g |
| 2-Ethoxyethanol | 2 g |
| Monoethanolamine | 1.2 g |
| Water q.s. | 100 g |
| pH 9 | |

When applied for 15 minutes at 30° C. on hair which has been bleached white, this mixture endows it, after shampooing and rinsing, with a golden chestnut coloration.

EXAMPLE 14

The following dyeing composition is prepared:

| | |
|---|---|
| 2-[3-Amino-2-(β-hydroxyethyl)amino-5-nitrophenyl]ethanol | 0.65 g |
| 3-Methylamino-4-nitrophenoxyethanol | 0.2 g |
| 3-Nitro-4-(β-hydroxyethyl)amino-N—methylaniline | 0.2 g |
| 2-Butoxyethanol | 10 g |
| ALFOL $C_{16/28}$ | 8 g |
| Lanette Wax E | 0.5 g |
| CEMULSOL B | 1 g |
| Oleic diethanolamide | 1.5 g |
| Monoethanolamine, 20% concentration by weight | 0.3 g |
| Water q.s. | 100 g |
| pH 9.5 | |

When applied for 20 minutes at 30° C. on bleached hair, this mixture endows it, after shampooing and rinsing, with a chestnut coloration.

EXAMPLE 15

The following dyeing composition is prepared:

| | |
|---|---|
| 1-(2,3-Diamino-5-nitrophenyl)-2-propanol | 0.1 g |
| 4-Amino-3-nitro-N—(β-hydroxyethyl)aniline | 0.06 g |
| 4-Methylamino-3-nitro-N,N—bis(β-hydroxyethyl)aniline | 0.08 g |
| 96° strength alcohol | 10 g |
| CARBOPOL 934 | 2 g |
| 5% strength ammonia solution | 4 g |
| Water q.s. | 100 g | pH 5

When applied for 20 minutes at 28° C. on light chestnut-coloured hair, this mixture endows it, after shampooing and rinsing, with a golden medium chestnut coloration.

EXAMPLE 16

The following dyeing composition is prepared:

| | |
|---|---|
| 1-(3-Amino-2-methylamino-5-nitrophenyl)-2-propanol | 0.08 g |
| 2-(β-Hydroxyethyl)amino-4-nitrophenoxyethanol | 0.07 g |
| N—(4-methylamino-3-chlorophenyl)-2-methyl-5-ureidobenzoquinoneimine | 0.06 g |
| N—{4-[ethyl(carbamylmethyl)amino]phenyl}-2-methyl-5-ureidobenzoquinoneimine | 0.052 g |
| 96° strength alcohol | 10 g |
| ALFOL C$_{16/18}$ | 8 g |
| Lanette Wax E | 0.5 g |
| CEMULSOL B | 1 g |
| Oleic diethanolamide | 1.5 g |
| Triethanolamine, 5% concentration by weight | 3 g |
| Water q.s. | 100 g |
| pH 8 | |

When applied for 25 minutes at 35° C. on bleached hair, this mixture endows it, after shampooing and rinsing, with a golden medium chestnut coloration.

EXAMPLE 17

The following dyeing mixture is prepared:

| | |
|---|---|
| 2-(2,3-Diamino-5-nitrophenyl)ethanol | 0.33 g |
| Resorcinol | 0.1 g |
| meta-Aminophenol | 0.08 g |
| para-Phenylenediamine | 0.08 g |
| para-Aminophenol | 0.08 g |
| 3-Acetamido-2,6-dimethylphenol | 0.1 g |
| CEMULSOL NP 4 | 12 g |
| CEMULSOL NP 9 | 15 g |
| Polyglycerolated oleic alcohol (2 moles of glycerol) | 1.5 g |
| Polyglycerolated oleic alcohol (4 moles of glycerol) | 1.5 g |
| Propylene glycol | 6 g |
| TRILON B | 0.12 g |
| Ammonia solution, 22° Be | 11 g |
| Mercaptosuccinic acid | 0.4 g |
| Water q.s. | 100 g |
| pH 9.4 | |

At the time of use, 100 g of "20 volumes" hydrogen peroxide are added.

When applied for 30 minutes at 28° C. on hair which is naturally 90% white, this mixture endows it, after shampooing and rinsing, with a dark blonde coloration.

EXAMPLE 18

The following dyeing mixture is prepared:

| | |
|---|---|
| 1-(2,3-Diamino-5-nitrophenyl)-2-propanol | 0.65 g |
| para-Phenylenediamine | 0.21 g |
| Resorcinol | 0.16 g |
| 2,4-Diaminophenoxyethanol(dihydrochloride) | 0.075 g |
| 3-(β-Hydroxyethyl)amino-6-methylphenol | 0.15 g |
| CELLOSIZE WP 03 | 2 g |
| Ammonium lauryl sulphate | 5 g |
| 2-Butoxyethanol | 15 g |
| 96° strength alcohol | 5 g |
| Ammonia solution, 22° Be | 10 g |
| Ammonium thiolactate | 0.8 g |
| Water q.s. | 100 g |
| pH 10.4 | |

At the time of use, 100 g of "20 volumes" hydrogen peroxide are added.

When applied for 30 minutes at 28° C. on bleached hair, this mixture endows it, after shampooing and rinsing, with a light chestnut coloration.

EXAMPLE 19

The following dyeing mixture is prepared:

| | |
|---|---|
| 1-(3-Amino-2-methylamino-5-nitrophenyl)-2-propanol monohydrochloride | 0.12 g |
| para-Aminophenol | 0.06 g |
| 4-Methylaminophenol hemisulphate | 0.09 g |
| 2-Methoxy-5-aminophenol | 0.105 g |
| 7-Hydroxybenzomorpholine | 0.05 g |
| 4-[Ethyl(carbamylmethyl)amino]aniline | 0.1 g |
| CEMULSOL NP 4 | 21 g |
| CEMULSOL NP 9 | 24 g |
| Oleic acid | 4 g |
| 2-Butoxyethanol | 3 g |
| 96° strength ethanol | 10 g |
| MASQUOL DTPA | 2.5 g |
| Thioglycolic acid | 0.6 g |
| Ammonia solution, 22° Be | 10 g |
| Water q.s. | 100 g |
| pH 10 | |

At the time of use, 100 g of "20 volumes" hydrogen peroxide are added.

When applied for 30 minutes at 28° C. on bleached hair, the mixture endows it, after shampooing and rinsing, with an ashen sandy coloration.

EXAMPLE 20

The following dyeing mixture is prepared:

| | |
|---|---|
| 2-[3-Amino-2-(β-hydroxyethyl)amino-5-nitrophenyl]ethanol | 0.26 g |
| 4-[Bis(β-hydroxyethyl)amino]aniline dihydrochloride | 0.19 g |
| Resorcinol | 0.07 g |
| 4-Amino-2-chlorophenol hydrochloride | 0.07 g |
| 3-Carbamylmethylamino-6-methylphenol | 0.1 g |
| ALFOL C 16/18 | 8 g |
| Lanette Wax E | 0.5 g |
| CEMULSOL B | 1 g |
| Oleic diethanolamide | 1.5 g |
| MASQUOL DTPA | 2.5 g |
| Mercaptosuccinic acid | 0.5 g |
| Ammonia solution, 22° Be | 11 g |
| Water q.s. | 100 g |
| pH 10.4 | |

At the time of use, 80 g of "20 volumes" hydrogen peroxide are added.

When applied for 25 minutes at 30° C. on hair which has been bleached to a reddish colour, the mixture endows it, after shampooing and rinsing, with a golden light brown coloration.

EXAMPLE 21

The following dyeing composition is prepared:

| | |
|---|---|
| 2-(2,5-Diamino-3-nitrophenyl)ethanol | 0.54 g |
| 2-Butoxyethanol | 15 g |
| CELLOSIZE WP 03 | 2 g |

| (Tallow alkyl)dimethylhydroxyethylammonium chloride | 2 g |
|---|---|
| Monoethanolamine in 20% strength aqueous solution | 1 g |
| Water q.s. | |
| pH 9.8 | |

When applied on hair for 15 minutes at 30° C., this mixture endows it, after shampooing and rinsing, with a coloration:
7.5 R 5/10 on hair which has been bleached white
7.5 R 5.5/6 on hair which is naturally 90% white, these colours being expressed according to Munsell's notation.

EXAMPLE 22

The following dyeing composition is prepared:

| 1-(2,5-Diamino-3-nitrophenyl)-2-propanol | 0.3 g |
|---|---|
| 2-Butoxyethanol | 10 g |
| 96° strength alcohol | 5 g |
| CELLOSIZE WP 03 | 2 g |
| Ammonium lauryl sulphate | 5 g |
| Water q.s. | 100 g |
| pH 6.9 | |

When applied on hair for 20 minutes at 28° C., this mixture endows it, after shampooing and rinsing, with a coloration:
8 R 5/10 on hair which has been bleached white
7.5 R 5.5/6 on hair which is naturally 90% white, these colours being expressed according to Munsell's notation.

EXAMPLE 23

The following dyeing composition is prepared:

| 1-[2-Amino-5-(β-hydroxyethyl)amino-3-nitrophenyl]-2-propanol | 0.7 g |
|---|---|
| 96° strength alcohol | 10 g |
| ALFOL C$_{16/18}$ | 8 g |
| Lanette Wax E | 0.5 g |
| CEMULSOL B | 1 g |
| Oleic diethanolamide | 1.5 g |
| 5% strength ammonia solution q.s. pH 9.9 | |
| Water q.s. | 100 g |

When applied on hair for 10 minutes at 28° C., this mixture endows it, after shampooing and rinsing, with a coloration:
7.5 RP 4/9 on hair which has been bleached white
7.5 RP 5.5/4 on hair which is naturally 90% white, these colours being expressed according to Munsell's notation.

EXAMPLE 24

The following dyeing composition is prepared:

| 1-(2,5-Diamino-3-nitrophenyl)-2-propanol | 0.16 g |
|---|---|
| 2-Amino-3-nitrotoluene | 0.095 g |
| 3-Nitro-4-[(γ-hydroxypropyl)amino]aniline | 0.12 g |
| 1,4,5,8-Tetraaminoanthraquinone (Cibacete microdisperse sapphire blue) | 0.12 g |
| LAURAMIDE | 1.5 g |
| Lauric acid | 1 g |
| CELLOSIZE WP 03 | 5 g |
| Monoethanolamine | 2 g |
| Water q.s. | 100 g |
| pH 9.5 | |

When applied for 20 minutes at 28° C. on hair which is naturally 90% white, this mixture endows it, after shampooing and rinsing, with a coppery blonde coloration.

EXAMPLE 25

The following dyeing composition is prepared:

| 2-(2,5-Diamino-3-nitrophenyl)ethanol | 0.2 g |
|---|---|
| 2-Amino-3-nitrophenol | 0.15 g |
| 3-Nitro-4-methylamino-N—(β-aminoethyl)aniline hydrobromide | 0.08 g |
| 96° strength alcohol | 10 g |
| LAURAMIDE | 1.5 g |
| Lauric acid | 1 g |
| CELLOSIZE WP 03 | 5 g |
| Monoethanolamine | 2 g |
| Water q.s. | 100 g |
| pH 9.7 | |

When applied for 25 minutes at 28° C. on hair which has been bleached white, this mixture endows it, after shampooing and rinsing, with a reddish-copper coloration.

EXAMPLE 26

The following dyeing composition is prepared:

| 1-[2-Amino-5-(β-hydroxyethyl)amino-3-nitrophenyl]-2-propanol | 0.36 g |
|---|---|
| 3-Nitro-4-aminophenol | 0.13 g |
| 2-(β-Hydroxyethyl)amino-5-{4-[bis(β-hydroxyethyl)amino]anilino}-1,4-benzoquinone | 0.17 g |
| 96° strength alcohol | 20 g |
| CELLOSIZE WP 03 | 2 g |
| (Tallow alkyl)dimethylhydroxyethylammonium chloride | 2 g |
| Triethanolamine, 5% concentration | 0.2 g |
| Water q.s. | 100 g |
| pH 7.7 | |

When applied for 20 minutes at 28° C. on hair which is naturally 90% white, this mixture endows it, after shampooing and rinsing, with a coppery blonde coloration.

EXAMPLE 27

| 1-(2,5-Diamino-3-nitrophenyl)-2-propanol | 0.7 g |
|---|---|
| 1-[2-Amino-5-(β-hydroxyethyl)amino-3-nitrophenyl]-2-propanol | 0.06 g |
| 2,5-Diaminopyridine dihydrochloride | 0.05 g |
| para-Aminophenol | 0.08 g |
| α-Naphthol | 0.035 g |
| 7-Hydroxybenzomorpholine | 0.07 g |
| 1-(2,4-Diaminophenoxy)-2,3-propanediol hydrochloride | 0.04 g |
| N—(β-Methoxyethyl)-para-phenylenediamine dihydrochloride | 0.04 g |
| Polyglycerolated oleic alcohol (2 moles of glycerol) | 4.5 g |
| Polyglycerolated oleic alcohol (4 moles of glycerol) | 4.5 g |
| ETHOMEEN TO 12 | 4.5 g |
| COMPERLAN KD | 9 g |
| Propylene glycol | 4 g |
| 2-Butoxyethanol | 8 g |
| 96% o strength ethanol | 6 g |
| MASQUOL DTPA | 2 g |
| Hydroquinone | 0.15 g |

| | |
|---|---|
| Sodium bisulphite solution, 35° Be | 1.3 g |
| Ammonia solution, 22° Be | 10 g |
| Water q.s. | 100 g |
| pH 10.5 | |

At this time of use, 110 g of "20 volumes" hydrogen peroxide are added.

When applied for 20 minutes at 28° C. on hair which is naturally 90% white, the mixture endows it, after shampooing and rinsing, with an ash blonde coloration.

EXAMPLE 28

The following dyeing mixture is prepared:

| | |
|---|---|
| 1-[2-Amino-5-($\beta$-hydroxyethyl)amino-3-nitrophenyl]-2-propanol | 0.1 g |
| 2-[2-($\beta$-hydroxyethyl)amino-3,5-dinitrophenyl]-ethanol | 0.8 g |
| 2-Methylresorcinol | 0.06 g |
| para-Phenylenediamine | 0.05 g |
| 2,4-Diaminophenoxyethanol dihydrochloride | 0.03 g |
| CEMULSOL NP 4 | 21 g |
| CEMULSOL NP 9 | 24 g |
| Oleic acid | 4 g |
| 2-Butoxyethanol | 3 g |
| 96° strength ethanol | 10 g |
| MASQUOL DTPA | 2.5 g |
| Sodium bisulphite solution, 35° Be | 1 g |
| Ammonia solution, 22° Be | 10 g |
| Water q.s. | 100 g |
| pH 10.6 | |

At the time of use, 100 g of "20 volumes" hydrogen peroxide are added.

When applied for 30 minutes at 28° C. on bleached hair, the mixture endows it, after shampooing and rinsing, with a bluish-grey coloration.

EXAMPLE 29

The following dyeing mixture is prepared:

| | |
|---|---|
| 2-(2,5-Diamino-3-nitrophenyl)ethanol | 0.08 g |
| 2-[2-($\beta$-hydroxyethyl)amino-3,5-dinitrophenyl]ethanol | 0.07 g |
| para-Phenylenediamine | 0.06 g |
| Resorcinol | 0.035 g |
| 5-Acetamido-2-methylphenol | 0.09 g |
| 1-Phenyl-3-methyl-5-pyrazolone | 0.065 g |
| CARBOPOL 934 | 3 g |
| 96° strength alcohol | 11 g |
| 2-Butoxyethanol | 5 g |
| (Tallow alkyl)dimethylhydroxyethylammonium chloride | 2 g |
| TRILON B | 0.2 g |
| Ammonia solution, 22° Be | 10 g |
| Sodium bisulphite, 35° Be | 1 g |
| Water q.s. | 100 g |
| pH 10.2 | |

At the time of use, 100 g of "20 volumes" hydrogen peroxide are added.

When applied for 20 minutes at 28° C. on hair which is naturally 90% white, the mixture endows it, after shampooing and rinsing, with a pinkish dark blonde coloration.

EXAMPLE 30

The following dyeing mixture is prepared:

| | |
|---|---|
| 1-[2-Amino-5-($\beta$-hydroxyethyl)amino-3-nitrophenyl]-2-propanol | 0.08 g |
| para-Aminophenol | 0.09 g |
| 1,4-Diamino-2,6-dimethylbenzene dihydrochloride | 0.04 g |
| Resorcinol | 0.06 g |
| [2-Amino-4-($\beta$-hydroxyethyl)aminophenoxy]-ethanol dihydrochloride | 0.05 g |
| CELLOSIZE WP 03 | 2 g |
| Ammonium lauryl sulphate | 5 g |
| 2-Butoxyethanol | 15 g |
| 96° strength alcohol | 5 g |
| Ammonia solution, 22° Be | 10 g |
| Ammonium thiolactate | 0.8 g |
| Water q.s | 100 g |
| pH 10.1 | |

At the time of use, 120 g of "20 volumes" hydrogen peroxide are added.

When applied for 40 minutes at 30° C. on hair which is naturally 90% white, the mixture endows it, after shampooing and rinsing with a pearly light grey coloration.

The various trade names used in the above examples are clarified in greater detail below:

ALFOL C$_{16/18}$: cetyl/stearyl alcohol sold by Condeéa.

Lanette Wax E: partially sulphated cetyl/stearyl alcohol, sold by Henkel.

CEMULSOL B: ethoxylated castor oil, sold by Rhône-Poulenc.

CELLOSIZE WP 03: hydroxyethylcellulose, sold by UNION CARBIDE

LAURAMIDE: lauric acid monoethanolamide, sold by Witco.

ETHOMEEN TO 12: oxyethylenated oleylamine (12 moles of ethylene oxide), sold by ARMAK.

COMPERLAN KD: coconut fatty acid diethanolamide, sold by HENKEL.

MASQUOL DTPA: diethylenetriaminepentaacetic acid pentasodium salt, sold by PROTEX.

CEMULSOL NP 4: oxyethylenated nonylphenol (4 moles of ethylene oxide), sold by Rhône-Poulenc.

CEMULSOL NP 9: oxyethylenated nonylphenol (9 moles of ethylene oxide) sold by Rhone-Poulenc.

CARBOPOL 934: acrylic acid polymer of M.W. 2 to 3 million, sold by GOODRICH CHEMICAL COMPANY.

TRILON B: ethylenediamine tetraacetic acid.

TWEEN 80: polyoxyethylenated sorbitol mono-oleate.

We claim:

1. Compound of formula (I) below:

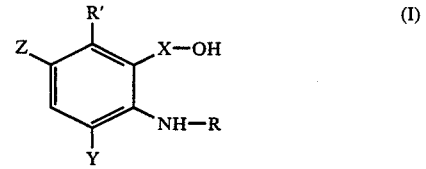

in which:
X denotes a branched or unbranched alkylene radical containing 2 to 6 carbon atoms, unsubstituted or substituted with one or more hydroxyl radicals;
R denotes a hydrogen, an alkyl or a mono- or polyhydroxyalkyl radical or an aminoalkyl radical in which the amine group can be mono- or disubstituted with an alkyl radical or with a mono- or polyhydroxyalkyl radical, and the alkyl radicals containing 1 to 4 carbon atoms; R' denotes a hydrogen atom or a $C_1$ to $C_4$ alkyl radical; Y and Z denote a nitro and/or —$NHR_1$ radical, $R_1$ and R, may be identical or different, $R_1$ having the meanings given above for R, with the proviso that when they are identical to each other, Y and Z both denote nitro radicals, and the cosmetically acceptable salts of the compounds containing a salifiable amine group.

2. 2,4-Dinitro-6-hydroxyalkylaniline of formula (I) according to claim 1 in which Y and Z denote a nitro radical, having the formula:

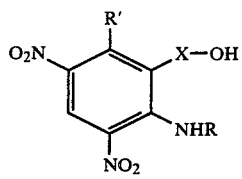
(Ia)

in which R', X or R have the meanings given above, and the cosmetically acceptable salts of the compounds containing a salifiable amine group.

3. Compound according to claim 1, in which R' is hydrogen or a methyl radical, X is chosen from the group consisting of ethylene, propylene, 1,1-dimethylethylene, 1,2-dimethylethylene and 1,1,2-trimethylethylene radicals and R is chosen from the group consisting of hydrogen and methyl, ethyl, n-propyl, β-hydroxyethyl, γ-hydroxypropyl, β,γ-dihydroxypropyl, β-aminoethyl and β-diethylaminoethyl radicals.

4. 2-Amino-4-nitro-6-hydroxyalkylaniline of formula (I) according to claim 1 in which Z denotes a nitro radical and Y an —$NHR_1$ radical, having the formula

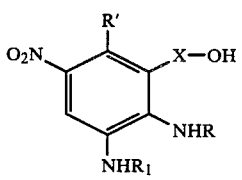
(Id)

in which R', X, R and $R_1$ have the meanings given in claim 1, or the cosmetically acceptable salts of the compounds containing a salifiable amine group.

5. Compound according to claim 4, in which R', in which R' is hydrogen or a methyl radical, X is chosen from the group consisting of ethylene, propylene, 1,1-dimethylethylene, 1,2-dimethylethylene or 1,1,2-trimethylethylene radicals and R and $R_1$ are chosen from the group consisting of hydrogen and methyl, ethyl, n-propyl, β-hydroxyethyl, γ-hydroxypropyl, β,γ-dihydroxypropyl, β-aminoethyl and β-diethylaminoethyl radicals.

6. 2-Nitro-4-amino-6-hydroxyalkylaniline of formula (I) according to claim 1 in which Y denotes a nitro radical and Z and —$NHR_1$ radical, having the formula

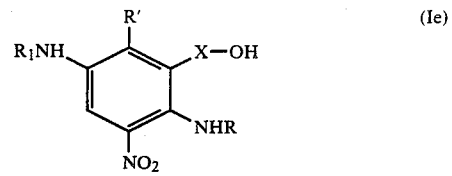
(Ie)

in which R', X, R and $R_1$ have the meanings given in claim 1, or the cosmetically acceptable salts of the compounds containing a salifiable amine group.

7. Compound according to claim 6, in which R' is hydrogen or a methyl radical, X is chosen from the group consisting of ethylene, propylene, 1,1-dimethylethylene, 1,2-dimethylethylene and 1,1,2-trimethylethylene radicals and R and $R_1$ are chosen from the group consisting of hydrogen and methyl, ethyl, n-propyl, β-hydroxyethyl, γ-hydroxypropyl, β,γ-dihydroxypropyl, β-aminoethyl and β-diethylaminoethyl radicals.

8. Compound according to claim 2, chosen from the group consisting of: 2-(2-amino-3,5-dinitrophenyl)ethanol, 2-[2-(β-hydroxyethyl)amino-3,5-dinitrophenyl]ethanol, 1-(2-amino-3,5-dinitrophenyl)-2-propanol, 1-(2-methylamino-3,5-dinitrophenyl)-2-propanol, 1-[2-(β-aminoethyl)amino-3,5-dinitrophenyl]-2-propanol or the salts of these compounds.

9. Compound according to claim 4, chosen from the group consisting of: 2-(2,3-diamino-5-nitrophenyl)ethanol, 2-[3-amino-2-(β-hydroxyethyl)amino-5-nitrophenyl]ethanol, 1-(2,3-diamino-5-nitrophenyl)-2-propanol, and 1-(3-amino-2-methylamino-5-nitrophenyl)-2-propanol or the salts of these compounds.

10. Compound according to claim 6, chosen from the group consisting of: 2-(2,5-diamino-3-nitrophenyl)ethanol, 1-(2,5-diamino-3-nitrophenyl)-2-propanol, and 1-[2-amino-5-(β-hydroxyethyl)amino-3-nitrophenyl]-2-propanol or the salts of these compounds.

11. Dyeing composition for human hair, which contains at least one compound as defined in claim 1 in a solvent medium.

12. Composition according to claim 11, which contains 0.0001 to 5% by weight of at least one compound of formula (I), relative to the total weight of the composition.

13. Composition according to claim 11, which has a pH of between 3 and 11.5.

14. Composition according to claim 11, in which the solvents are chosen from the group consisting of water, lower alkanols, aromatic alcohols, polyols, glycols or glycol ethers, and mixtures thereof.

15. Composition according to claim 11, which contains, in addition, cosmetic adjuvants chosen from the group consisting of anionic, cationic, nonionic or amphoteric surfactants or mixtures thereof, thickeners, dispersants, penetrants, sequestering agents, film-forming agents, buffers, perfumes and alkalinising or acidifying agents.

16. Composition according to claim 11, intended for use for direct dyeing of human hair, which contains, in addition, other direct dyes chosen from the group consisting of azo dyes, anthraquinone dyes, indophenols, indoanilines and nitro derivatives of the benzene series other than those of formula (I).

17. Composition according to claim 11, intended for use as a hair setting lotion, which takes the form of an aqueous, alcoholic or hydroalcoholic solution containing at least one cosmetic resin.

18. Composition according to claim 11, intended for use for oxidation dyeing, which contains in addition at least one oxidation dye precursor.

19. Composition according to claim 18, which has a pH of between 7 and 11.5, and which contains, in addition, a reducing agent.

20. Process for dyeing human hair, which consists in applying a composition as defined in claim 11 on the fibres, in leaving the composition in place for 5 to 50 minutes, and then rinsing the fibres, optionally washing them, rinsing again and drying them.

21. Process for dyeing human hair, which consists in applying a composition as defined in claim 17 on the fibres which have been washed and rinsed, optionally coiling the fibres and drying them.

22. Process for dyeing human hair, which consists in applying on the fibres a composition as defined in claim 18, to which an oxidising agent is optionally added, in leaving the composition in place for 10 to 50 minutes, and in rinsing the fibres, optionally washing them with shampoo, rinsing again and drying them.

23. Composition according to claim 15, which contains 0.05 to 2%, by weight of at least one compound of formula (I), relative to the total weight of the composition.

* * * * *